US00PP21737P2

(12) United States Plant Patent
Slaughter et al.

(10) Patent No.: US PP21,737 P2
(45) Date of Patent: Mar. 1, 2011

(54) PEACH TREE NAMED 'BURPEACHTWENTYFOUR'

(50) Latin Name: *Prunus persica*
Varietal Denomination: Burpeachtwentyfour

(75) Inventors: John K. Slaughter, Fresno, CA (US); Timothy J. Gerdts, Kingsburg, CA (US)

(73) Assignee: The Burchell Nursery, Inc., Oakdale, CA (US)

( * ) Notice: Subject to any disclaimer, the term of this patent is extended or adjusted under 35 U.S.C. 154(b) by 0 days.

(21) Appl. No.: 12/653,502

(22) Filed: Dec. 14, 2009

(51) Int. Cl.
*A01H 5/00* (2006.01)

(52) U.S. Cl. ..... Plt./195
(58) Field of Classification Search ..... Plt./195

See application file for complete search history.

*Primary Examiner*—Kent L Bell
(74) *Attorney, Agent, or Firm*—Wells St. John P.S.

(57) ABSTRACT

A new and distinct variety of Peach tree (*Prunus persica*), which is denominated varietally as 'Burpeachtwentyfour', and which produces an attractively colored white-fleshed, clingstone peach which is mature for harvesting and shipment approximately May 16 to May 23 under the ecological conditions prevailing in the San Joaquin Valley of central California.

1 Drawing Sheet

BACKGROUND OF THE NEW VARIETY

The present invention relates to a new, novel and distinct variety of peach tree, *Prunus persica*, and which has been denominated varietally as 'Burpeachtwentyfour'.

ORIGIN

The present variety of peach tree resulted from an on-going program of fruit and nut tree breeding. The purpose of this program is to improve the commercial quality of deciduous fruit and nut varieties, and rootstocks, by creating and releasing promising selections of *Prunus, Malus* and *Regia* species. To this end we make both controlled and hybrid cross pollinations each year in order to produce seedling populations from which improved progenies are evaluated and selected.

The seedling, 'Burpeachtwentyfour' was originated by us and selected from a population of seedlings growing in our experimental orchards located near Fowler, Calif. The seedlings, grown on their own roots, were derived from a cross that we made in 2000 of the 'Queencrest' peach tree (U.S. Plant Pat. No. 6,025), which is an early ripening, yellow-fleshed, clingstone peach tree which was used as the seed parent; and an unnamed white fleshed flat (peento) peach tree of unknown origin, and which was used as the pollen parent. The seeds produced by this cross were embryo cultured, in vitro, and then subsequently grown in a greenhouse to an appropriate stage. Subsequently, the new plants were field planted and grown for further evaluation. One seedling which is the present variety, exhibited especially desirable characteristics, and was designated as 'J47.083'. This seedling was marked for subsequent observation. After the 2002 fruiting season, the new variety of peach tree was selected for advanced evaluation and repropagation.

ASEXUAL REPRODUCTION

Asexual reproduction of this new and distinct variety of peach tree was accomplished by budding the new peach tree to 'Nemaguard' Rootstock (un-patented) during the 2003 growing season. This was performed by us in our experimental orchard which is located near Fowler, Calif. Subsequent evaluations of these asexually reproduced plants have shown those asexual reproductions run true to the original tree. All characteristics of the original tree, and its fruit, were established, and appear to be transmitted through succeeding asexual propagations.

SUMMARY OF THE VARIETY

'Burpeachtwentyfour' is a new and distinct variety of peach tree, which produces fruit which are considered of relatively large size, and which further has vigorous growth. This new peach tree is also a regular and productive bearer of firm, white-fleshed, clingstone fruit which have a good flavor and eating qualities. This new peach tree has a medium chilling requirement of approximately 650 hours, and further produces relatively uniformly shaped fruit throughout the tree. In addition to the foregoing, the fruit of the new tree also appears to have good handling and shipping qualities.

The 'Burpeachtwentyfour' peach tree bears fruit which are ripe for commercial harvesting and shipment on approximately May 16 to May 23 under the ecological conditions prevailing in the San Joaquin Valley of central California. In relative comparison to the 'Queencrest' peach tree (U.S. Plant Pat. No. 6,025), which was the seed parent, and the most similar variety known to the inventors at this time, the present, new variety of peach tree bears fruit which ripen about at about the same time of the season, but which is white-fleshed (as opposed to yellow-fleshed) and considerably firmer when both peach trees have been grown and evaluated at the same geographical location and using the same cultural practices.

BRIEF DESCRIPTION OF THE DRAWING

The accompanying drawing, which is provided, is a color photograph of the new peach tree variety. The photograph depicts two whole mature fruit, and one mature fruit bisected laterally along the mid-equatorial plane, and which reveals the flesh characteristics thereof. The external coloration of the fruit as shown in the photograph is sufficiently matured for harvesting and shipment. Additionally, the photograph displays a sample vegetative shoot bearing typical leaves and a typical stone, with the flesh removed to display the characteristics thereof. The colors in this photograph are as nearly true as is reasonably possible in a color representation of this type. Due to chemical development, processing and printing, the leaves and fruit depicted in these photographs may or may not be accurate when compared to the actual specimen. For this reason, future color references should be made to the color plates (Royal Horticultural Society) and descriptions provided, hereinafter.

DETAILED DESCRIPTION

Referring more specifically to the pomological details of this new and distinct variety of peach tree, the following has been observed during the fifth fruiting season under the ecological conditions prevailing at orchards which are located near the town of Fowler, county of Fresno, state of California. All major color code designations are by reference to The R.H.S. Colour Chart (Fourth Edition) provided by The Royal Horticultural Society of Great Britain. Common color names are also occasionally used.

Tree:

*Size.*—Generally — Considered large as compared to other common commercial peach cultivars ripening in the early season of maturity. The tree of the present variety (which was 5 years old) was pruned to a height of approximately 350.0 cm. to about 355.0 cm. at commercial maturity.

*Vigor.*—Considered vigorous. The present peach tree variety grew from about 160.0 cm. to about 165.0 cm. in height during the first growing season. The new variety was pruned to a height of approximately 150.0 cm. during the first dormant season, and primary scaffolds were then selected for the desired tree structure.

*Productivity.*—Productive. Fruit set varies from about 2.5 to several times more than the desired crop load. The fruit set is spaced by thinning to develop the remaining fruit into the desired market-sized fruit. The number of the fruit set varies with the prevailing climatic conditions, and cultural practices employed during the bloom period, and is therefore not distinctive characteristics of the variety.

*Bearer.*—Regular. Fruit set has been heavy during the last several years of observation, and thinning was periodically necessary during the past 5 years on both the original seedling and also on the subsequent propagations of the new tree.

*Form.*—Upright, and pruned into a vase shape.

*Density.*—Considered dense. It has been discovered that pruning the branches from the center of the tree to obtain a resulting vase-shape allows for air movement and appropriate amounts of sunlight to enhance the fruit color, and the renewal of fruiting wood throughout the tree.

*Hardiness.*—The present peach tree was grown and evaluated in USDA Hardiness Zone 9. Winter chilling requirements of the new tree have been calculated as approximately 650 hours below 7.0 degrees C. The present variety appears to be hardy under typical central San Joaquin Valley climatic conditions. Because of its lower chilling requirement the present variety of peach tree appears that it could be suitably grown in climates that have fewer chilling hours than that of USDA Hardiness Zone 9.

Trunk:

*Diameter.*—Approximately 13.5 cm. in diameter when measured at a distance of approximately 15.24 cm. above the soil level. This measurement was taken at the end of the fifth growing season.

*Bark texture.*—Considered moderately rough, with numerous folds of papery scarfskin being present.

*Lenticels.*—Generally — Very numerous flat, oval lenticels are present. The lenticels have a size of approximately 3.0 millimeters in width, and about 1.0 millimeter in height. The development and size of the observed lenticels can be influenced by prevailing growing conditions. Therefore, this characteristic is not necessarily a consistent and dependable descriptor of the variety.

*Lenticel color.*—Considered an orange brown, (RHS Greyed-Orange Group N172 D).

*Bark coloration.*—Variable, but it is generally considered to be a medium brown, (RHS Greyed-Brown Group N199 C). The present bark description was taken from trees in their fifth leaf which have not as yet ruptured the scarf skin nor developed bark furrowing. These characteristics are more typical of older trees.

Branches:

*Size.*—Considered medium for the variety.

*Diameter.*—Average as compared to other peach tree varieties. The branches of the present tree have a diameter of about 8.5 centimeters when measured during the fifth year after grafting.

*Surface texture.*—Average, and appearing furrowed on wood which is several years old.

*Crotch angles.*—Primary branches are considered variable and are between about 57 degrees to about 58 degrees when measured from a horizontal axis. This particular characteristic is not considered distinctive of the variety, however.

*Current season shoots.*—Surface texture — Substantially glabrous.

*Internode length.*—Approximately 2.6 cm.

*Color of mature branches.*—Grey-brown, (RHS Greyed-Brown group 199 B).

*Current seasons shoots.*—Color — Light green, (RHS Yellow-Green Group 144 B). The color of new shoot tips is considered a bright and shiny green (RHS Green Group 141 C).

Leaves:

*Size.*—Considered medium-large for the species. Leaf measurements have been taken from vigorous, upright, current-season growth at approximately mid-shoot.

*Leaf length.*—Approximately 176.0 mm. to about 184.0 mm.

*Leaf width.*—Approximately 32.0 mm. to about 35.0 mm.

*Leaf base shape.*—Considered reasonably uniform in marginal symmetry when viewed relative to the leaf longitudinal axis.

*Leaf form.*—Lanceolate.

*Leaf tip form.*—Acuminate.

*Leaf color.*—Upper Leaf Surface — Dark green, (approximately RHS Green Group 137 A).

*Leaf texture.*—Glabrous.

*Leaf color.*—Lower Surface — Deep green, (approximately RHS Green Group 139 B).

*Leaf venation.*—Pinnately veined.

*Mid-vein.*—Color — Considered a light yellow-green, (approximately RHS Yellow-Green Group 145 B) in the early, to mid period, of the growing season.

*Leaf margins.*—Shape — Slightly undulating. Marginal form. — Considered blunted-serrate, occasionally biserrate. Uniformity. — Considered generally uniform.

*Leaf petioles.*—Form. — Considered canaliculate but with a shallow channel and thicker trough. Leaf Petiole Size. — Considered medium. Leaf Petiole Length. — About 8.0 mm. to about 12.0 mm. Leaf Petiole diameter. — About 1.5 mm. to about 2.0 mm. Leaf Petiole Color. — Pale green, (approximately RHS Yellow-Green Group N144 C).

*Leaf glands.*—Size — Considered small. Approximately 1.0 mm. in length, and about 1.0 mm. in height. Leaf Gland Number. — Generally one gland per margin side. Occasionally two glands per margin side. Type. — Generally considered a tight, small reniform gland acutely appressed relative to the apical leaf margin. Leaf Gland Color. — Considered a pale green approximately (RHS Yellow-Green Group 144 C).

*Leaf stipules.*—Size — Medium large for the variety. Number. — Typically 2 per leaf bud and up to 6 per shoot tip. Leaf Stipules. — Form — Lanceolate and having a serrated margin. Leaf Stipules. — Color — Green, (approximately RHS Green Group 137 B) when young, but turning to a brown color, (approximately RHS Greyed-Orange group 174 C) with advancing senescence. The stipules are considered to be early deciduous.

Flowers:

*Flower buds.*—Generally — Depending upon the stage of development, the flower buds are approximately 6.0 mm. wide; about 10.0 mm. long; conic in form; and slightly appressed relative to the bearing shoot.

*Flower buds.*—Color — This characteristic is dependent upon the proximity to bloom. The bud scales are typically deep purple, (approximately RHS Greyed-Purple Group N186 C). The buds are considered hardy under typical central San Joaquin Valley climatic conditions.

*Hardiness.*—No winter injury (bud death) has been noted during the last several years of evaluation in the central San Joaquin Valley. The current variety has not been intentionally subjected to drought or heat stress, and therefore this information is not available.

*Date of first bloom.*—Observed on Feb. 24, 2008.

*Blooming time.*—Considered early in relative comparison to other commercial peach cultivars grown in the central San Joaquin Valley. The date of full bloom was observed on Mar. 1, 2008. The date of full bloom varies slightly with the current climatic conditions and prevailing cultural practices.

*Duration of bloom.*—Approximately 8 days. This characteristic varies slightly with the prevailing climatic conditions.

*Flower type.*—The variety is considered to have a showy type flower.

*Flower size.*—The flower diameter at full bloom is approximately 33.0 mm. to about 38.0 mm.

*Bloom quantity.*—Considered abundant.

*Flower bud frequency.*—Normally 2 flower buds appear per node, occasionally one, but rarely more than 2.

*Petal size.*—Generally — Considered medium for the species. Length. — Approximately 12.0 mm. to about 15.0 mm. Width. — Approximately 11.0 mm. to about 14.0 mm.

*Petal form.*—Considered ovate.

*Petal count.*—Nearly always 5.

*Petal texture.*—Glabrous.

*Petal color.*—Somewhat variable from a light pink, (approximately RHS Red-Purple Group 65 C) to a medium pink, (approximately RHS Red-Purple Group 65 A).

*Fragrance.*—Slight.

*Petal claw.*—Form — The claw is considered generally ovoid, and has a small size when compared to other varieties. Petal Claw Length. — Approximately 6.0 mm. to about 8.0 mm. Petal Claw Width. — Approximately 6.0 mm. to about 8.0 mm.

*Petal margins.*—Generally considered variable, from nearly smooth to slightly ruffled, and occasionally moderately undulate to ruffled.

*Petal apex.*—Generally considered acute — The petal apices generally exhibit a slight and rounded tip.

*Flower pedicel.*—Length — Considered medium-long, and having an average length of approximately 4.0 mm. to about 5.0 mm. Flower Pedicel Diameter. — Considered average, approximately 2.5 millimeters. Flower Pedicel Color. — A medium brown, (approximately RHS Grey-Brown Group N199 C).

*Floral nectaries.*—Color — A dull green, (approximately RHS Yellow-Green Group 144 C).

*Calyx.*—Surface Texture — Generally glabrous. Floral Nectaries. — Color — A dull purple, (approximately RHS Greyed-Red Group 178 C).

*Sepals.*—Surface Texture — The surface of the sepals have a short, fine pubescent texture. Sepals Size. — Average, and ovate in form. Sepals Color. — A dull red, (approximately RHS Greyed-Green Group 197 C).

*Anthers.*—Generally — Average in length. Anthers Color. — Depending upon the date of maturity and this date's proximity to dehistance. The pre-dehistant color is considered a dull magenta, (approximately RHS Greyed-Red Group 182 A).

*Pollen production.*—Pollen is abundant, and has a yellow color, (approximately RHS Yellow-Orange Group 17 C).

*Fertility.*—No pollinator is required.

*Filaments.*—Size — The length dimension is variable, approximately 13.0 mm. to about 17.0 mm. long. Filaments Color. — Considered white, (approximately RHS White Group 155 C).

*Pistil.*—Number — Usually 1 occasionally 2, but rarely more than 2. Pistil Size. — Average. Pistil Length. — Approximately 17.0 mm. to about 20.0 mm. including the ovary. Pistil Color. — Considered a very pale green, (approximately RHS Greyed-Green Group 193 C). Pistil Surface Texture. — The variety has a long pubescent pistil.

Fruit:

*Maturity when described.*—Firm ripe condition (shipping ripe).

*Date of first picking.*—May 16, 2008. Date of last picking. — May 23, 2008. The date of harvest varies slightly with the prevailing climatic conditions.

*Fruit size.*—Generally — Considered large, and uniform.

*Average cheek diameter.*—Approximately 63.0 mm. to about 70.0 mm.

*Average axial diameter.*—Approximately 64.0 mm. to about 69.0 mm.

*Typical weight.*—Approximately 209.0 grams. This characteristic is highly dependent upon the prevailing cultural practices, and therefore is not particularly distinctive of the variety.

*Fruit form.*—Generally — Considered rounded. The fruit is generally uniform in symmetry. It should be noted that occasional asymmetry can occur in the axial hemispheres of the fruit.

*Fruit suture.*—The suture is full, but well defined along its margin with no apparent grooving or depression. No readily apparent callousing or stitching exists along the suture line.

*Fruit suture.*—Color — Generally blushed to the same degree as the skin, (approximately RHS Red Group 46 B).

*Ventral surface.*—Form — Even and uniform into the stem cavity with occasional creasing noted at the ventral portion of the of the shoulder.

*Apex.*—Shape — Rounded.

*Base.*—Shape — Gently retuse.

*Stem cavity.*—Shape — Generally rounded and uniform. Average depth of the stem cavity is about 5.0 mm. Average width of the stem cavity is about 8.0 mm.

*Fruit skin.*—Thickness — Considered medium in thickness, and tenacious to the flesh. Fruit Skin Texture. — Short, fine and pubescent. The pubescence is moderately abundant. Fruit Skin Taste. — Non-astringent. Tendency to crack. — None observed in the previous years of evaluation in the Southern San Joaquin Valley.

*Fruit skin.*—Blush Color — Generally speaking, a red blush exists on a majority of the skin of the fruit (approximately RHS Red Group 44 A), and is typically more present on the portions of the fruit having direct sunlight exposure. The blush covers approximately 80-90% of the fruit skin surface. The percentage of the blush color on the fruit skin surface can vary, and is generally dependent upon the fruit's direct exposure to sunlight; specific fruit maturity; and the prevailing ecological and cultural conditions under which the fruit is being grown. Fruit Skin Ground Color. — Yellow, (approximately RHS Yellow-Orange Group 16 D). The ground color of the fruit skin can vary significantly relative to the maturity date of the fruit when this measurement is taken.

*Fruit stem.*—Length — approximately 6.0 mm. to about 8.0 mm. Fruit Stem Diameter. — Approximately 2.0 mm. to about 3.0 mm. Fruit Stem Color. — Pale yellow-green, (approximately RHS Yellow-Green Group N144 D).

*Flesh.*—Ripening. — Considered even. Flesh Texture. — Firm, juicy and dense. Considered non-melting. Flesh Fibers. — A few are found. Flesh Aroma. — Very slight. Flesh Eating Quality. — Considered very good. Flesh Flavor. — Considered sweet and with low acidity. The flavor is considered both pleasant and balanced.

*Juice production.*—Moderate.

*Brix.*—About 14.0 degrees to 18.0 degrees. This characteristic varies slightly with the number of fruit per tree; maturity of fruit when harvested; prevailing cultural practices; and the surrounding climatic conditions.

*Flesh color.*—White, (approximately RHS Yellow Group 2D).

Stone:

*Stone type.*—Clingstone.

*Stone size.*—Considered medium-large for the variety. The stone size varies significantly depending upon the tree vigor, crop load and prevailing growing conditions.

*Stone length.*—Average, about 27.0 mm. to about 31.0 mm.

*Stone width.*—Average, about 22.0 mm. to about 25.0 mm.

*Stone diameter.*—Average, about 15.0 mm. to about 18.0 mm.

*Stone form.*—Ovoid.

*Stone base.*—The stone is usually rounded and considered narrow or slightly elongated.

*Stone apex.*—Shape — The stone apex is slightly lobed and generally has a prominent apical tip.

*Stone surface texture.*—Generally speaking the stone of the present variety normally does not have sufficient time to develop and mature as compared to the stones of medium or later ripening peach varieties. Therefore, the stone is lighter color, more porous and less dense than stones of medium and late season varieties which have had more time to develop, harden and lignify. Surface pitting is generally more noted toward the dorsal edges of the stone. Larger and more elongated pits are generally noted nearer the stones apex, and smaller pits are generally found nearer the stone base. Ridges. — Ridging is generally more prominent at locations which are parallel and laterally disposed relative to the ventral margin. Ventral Edge. — Shape — The ventral edge is generally considered moderately smooth with even labia bracketing the ventral suture. Dorsal Edge. — Shape — Generally considered moderately rough and uneven. Folds of surface ridges on the external margins often end abruptly along the external margin of the dorsal surface creating an irregular edge.

*Stone color.*—The color of the dry stone is generally considered a pale yellow white, (approximately RHS Greyed-Orange Group 164 A). This color is variable however, and may be affected by oxidation and moisture content. In view of this variability, this particular characteristic cannot be considered distinctive of the variety.

*Tendency to split.*—Splitting has occasionally been noted.

*Kernel.*—Size — Medium-small. Kernel Form. — Considered generally ovoid but as the immature embryo and its cotyledons have not fully developed, the kernel form is generally considered shriveled and underdeveloped especially on the basal end.

Pellicle. — Slightly pubescent. Kernel Color. — (RHS Yellow-Orange Group 19 D).

*Fruit use.*—The subject variety which is named 'Burpeachtwentyfour' is considered to be a peach tree of the early season of maturity, and which produces fruit which are considered to be firm, attractively colored, and which are useful for both local and long distance shipping.

*Keeping quality.*—Appears excellent. The fruit of the present variety has stored well for up to 30 days after harvest at 1.0 degree Celsius.

*Shipping quality.*—Good. The fruit produced by the new peach tree variety showed minimal bruising of flesh or skin damage after being subjected to normal harvesting and packing procedures.

*Resistance to insects and disease.*—No particular susceptibilities were noted. The present peach tree variety has not been tested to expose or detect any susceptibilities or resistances to any known plant and/or fruit diseases.

Although the new variety of peach tree possesses the described characteristics when grown under the ecological conditions prevailing near Fowler, Calif., in the Central part of the San Joaquin Valley of California, it should be understood that variations of the usual magnitude and characteristics incident to changes in growing conditions, fertilization, pruning, pest control, frost, climatic variables and horticultural management practices are to be expected.

Having thus described and illustrated our new variety peach tree, what we claim is new and desire to secure by Plant Letters Patent is:

1. A new distinct variety of Peach tree, substantially as illustrated and described, and which is characterized principally as to novelty by producing an attractively colored white-fleshed, clingstone peach which is mature for harvesting and shipment approximately May 16 to May 23 under the ecological conditions prevailing in the San Joaquin Valley of central California.

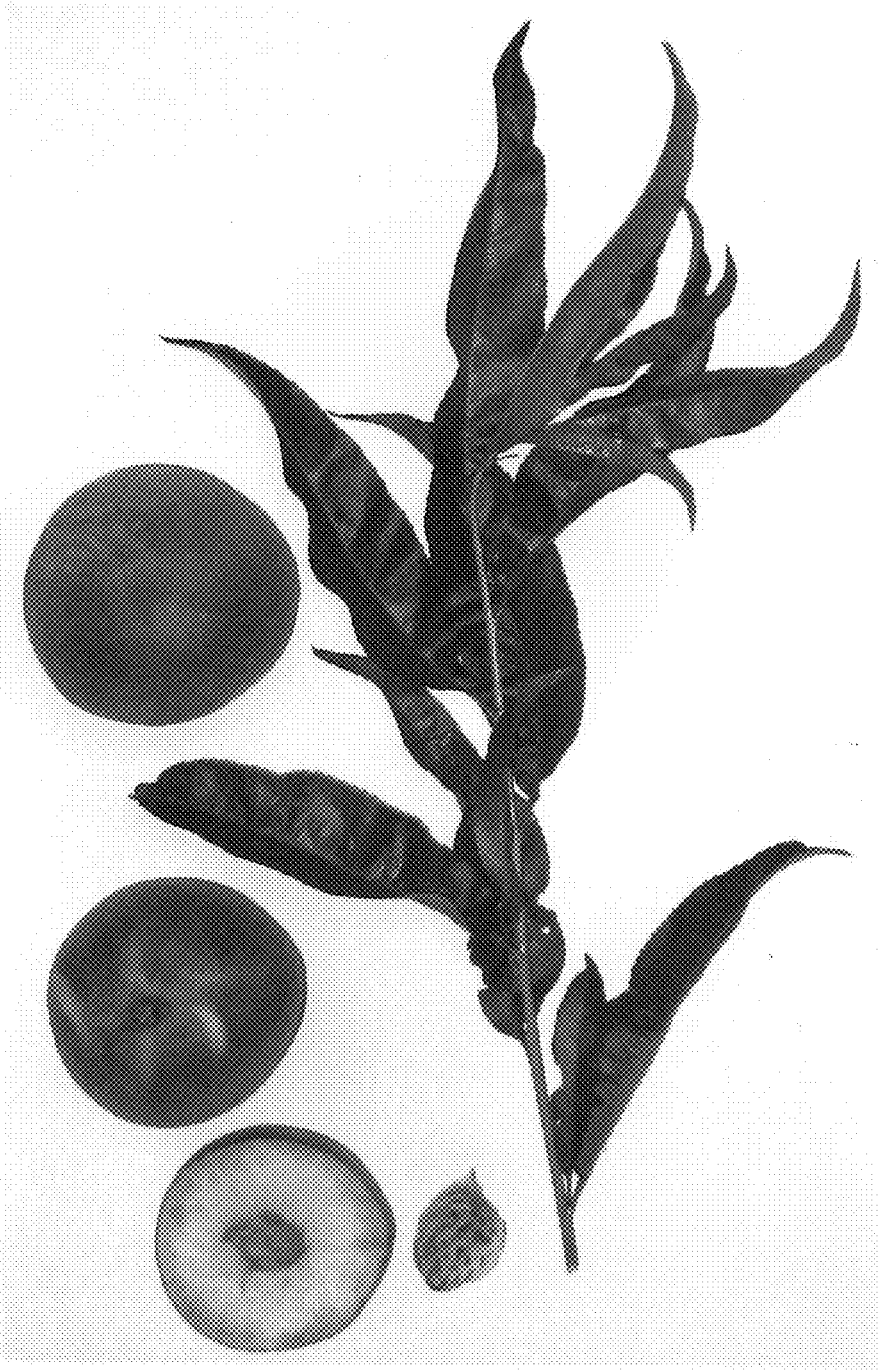

* * * * *